United States Patent
Iwasaki et al.

(10) Patent No.: US 8,355,135 B2
(45) Date of Patent: Jan. 15, 2013

(54) SURFACE PLASMON RESONANCE MEASURING DEVICE, SAMPLE CELL, AND MEASURING METHOD

(75) Inventors: Yuzuru Iwasaki, Kanagawa (JP); Tsutomu Horiuchi, Kanagawa (JP); Michiko Seyama, Kanagawa (JP); Toru Miura, Kanagawa (JP); Tsuneyuki Haga, Kanagawa (JP); Tsuyoshi Hayashi, Kanagawa (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 377 days.

(21) Appl. No.: 12/812,219

(22) PCT Filed: Jan. 16, 2009

(86) PCT No.: PCT/JP2009/050564
§ 371 (c)(1),
(2), (4) Date: Jul. 8, 2010

(87) PCT Pub. No.: WO2009/091039
PCT Pub. Date: Jul. 23, 2009

(65) Prior Publication Data
US 2010/0284013 A1    Nov. 11, 2010

(30) Foreign Application Priority Data
Jan. 16, 2008  (JP) .................. 2008-006647
Jan. 16, 2008  (JP) .................. 2008-006649

(51) Int. Cl.
*G01N 21/55* (2006.01)
*H03M 1/22* (2006.01)
(52) U.S. Cl. ............... 356/445; 341/1; 356/448
(58) Field of Classification Search .......... 356/445–448, 356/450–458
See application file for complete search history.

(56) References Cited

U.S. PATENT DOCUMENTS

| | | | | |
|---|---|---|---|---|
| 4,847,474 A * | 7/1989 | Engel et al. | .............. | 235/462.14 |
| 6,006,995 A * | 12/1999 | Amundsen et al. | ...... | 235/462.32 |
| 6,642,062 B2 * | 11/2003 | Kauvar et al. | ................. | 436/518 |
| 6,758,391 B1 * | 7/2004 | Pickens, III | ................... | 235/375 |
| 6,869,763 B1 | 3/2005 | Tamura et al. | | |
| 7,559,475 B2 * | 7/2009 | Kotlarsky et al. | ........ | 235/462.42 |

(Continued)

FOREIGN PATENT DOCUMENTS
DE        100 42 797 A1    3/2002

(Continued)

OTHER PUBLICATIONS

"Integrated Fluid Handling System for Biomolecular Interaction Analysis", Analytical Chemistry, 1991, vol. 63, No. 29, pp. 2338-2345.

*Primary Examiner* — Gregory J Toatley
*Assistant Examiner* — Jarreas C Underwood
(74) *Attorney, Agent, or Firm* — Blakely, Sokoloff, Taylor & Zafman

(57) ABSTRACT

A surface plasmon resonance measuring device includes a light source (2) which irradiates, with condensed light, a sample cell (10) having the characteristic structure of the reflectance of light that is formed in advance as a code from at least either of a substance film to be measured and a substance film different from the substance film to be measured, from a surface opposite to one on which the substance film to be measured is immobilized to a metal thin film, a CCD camera (5) which detects light reflected by the sample cell (10), and a data processing device (6) which extracts the identification code of the sample cell (10) from the feature of an image sensed by the camera (5).

27 Claims, 15 Drawing Sheets

U.S. PATENT DOCUMENTS

| | | |
|---|---|---|
| 2004/0191815 A1 | 9/2004 | Kyo et al. |
| 2005/0064435 A1* | 3/2005 | Su et al. ............... 435/6 |
| 2005/0227271 A1 | 10/2005 | Kwon |

FOREIGN PATENT DOCUMENTS

| | | |
|---|---|---|
| EP | 1 388 587 A1 | 2/2004 |
| JP | 2000-338110 A | 12/2000 |
| JP | 2001-194298 A | 7/2001 |
| JP | 3356213 B | 4/2002 |
| JP | 2005-069787 A | 3/2005 |
| JP | 2005-300543 A | 10/2005 |
| WO | WO 2005/024695 A2 | 3/2005 |
| WO | WO 2007/105771 A2 | 9/2007 |
| WO | WO 2007/145180 A1 | 12/2007 |

* cited by examiner

INCIDENT ANGLE

SURFACE PLASMON RESONANCE MEASURING DEVICE, SAMPLE CELL, AND MEASURING METHOD

This is a non-provisional application claiming the benefit of International application number PCT/JP2009/050564 filed Jan. 16, 2009.

TECHNICAL FIELD

The present invention relates to a surface plasmon resonance measuring device which quantitatively or qualitatively measures a specific substance using an optical system.

BACKGROUND ART

These days, surface plasmon resonance (to be referred to as SPR) measuring devices have been studied as a biosensor using light (see, e.g., Japanese Patent Laid-Open No. 2001-194298, Japanese Patent No. 3356213, and reference: "'Integrated Fluid Handling System for Biomolecular Interaction Analysis', Analytical Chemistry, 1991, Vol. 63, No. 20, pp. 2338-2345"). The SPR measuring device uses a measurement sample cell obtained by immobilizing a substance film to be measured, such as an antibody, to a metal thin film made of gold, silver, or the like. The sample cell is irradiated with light from a surface opposite to the antibody. The SPR measuring device measures an incident angle at which the evanescent wave of the light and the surface plasmon wave resonate with each other.

FIG. 34 is a block diagram showing the schematic arrangement of a conventional SPR measuring device. The SPR measuring device includes a prism 1001, light source 1002, polarizing plate 1003, condenser lens 1004, and CCD camera 1005.

When light emitted by the light source 1002 for monochromatic light reaches the polarizing plate 1003, only p-polarized light passes. The p-polarized light is condensed by the condenser lens 1004 and enters the semi-columnar or hemispherical prism 1001. A sample cell 1000 is set on the upper surface of the prism 1001. The p-polarized light enters the sample cell 1000 from a surface opposite to one on which a substance film to be measured such as an antibody is immobilized. The p-polarized light enters the sample cell 1000 at the incident angle θ via the prism 1001. The CCD camera 1005 detects an intensity change of the light reflected by the sample cell 1000.

Light emitted by the light source 1002 becomes an evanescent wave at the boundary between the prism 1001 and the metal thin film of the sample cell 1000. A surface plasmon wave is generated on the surface of the metal thin film. At the incident angle θ at which the wave numbers of the evanescent wave and surface plasmon wave match each other, the evanescent wave is used for excitation of the surface plasmon wave, decreasing the quantity of light measured as reflected light. At this time, the CCD camera 1005 measures the intensity of the reflected light, observing a decrease in reflectance at the incident angle at which the evanescent wave and surface plasmon wave resonate with each other, as shown in FIG. 35. On an incident angle-reflectance curve representing the relationship between the incident angle and the reflectance, a low-reflectance valley appears near the incident angle at which the evanescent wave and surface plasmon wave resonate with each other.

The angle at which the evanescent wave and surface plasmon wave resonate with each other depends on the refractive index of a substance film to be measured in contact with the metal thin film of the sample cell 1000. When the substance film to be measured such as an antibody is immobilized on the metal thin film, the refractive index of the antibody changes owing to antigenic binding, and the angle at which the valley appears slightly changes. By measuring this change, the substance film to be measured can be quantified.

DISCLOSURE OF INVENTION

Problems to be Solved by the Invention

However, the conventional SPR measuring device may generate a measurement error. The first reason of the measurement error is that the conventional SPR measuring device cannot identify a sample cell. Sample cells each prepared by immobilizing an antibody or the like on a metal thin film are similar in appearance. When many sample cells are used, they may be confused. To prevent this, for example, the conventional SPR measuring device marks a sample cell. However, the work is very cumbersome and an error readily occurs.

The second reason of the measurement error is that the conventional SPR measuring device cannot detect whether an appropriate liquid sample flows on the sample cell. The SPR measuring device pumps a liquid sample such as milk to flow on the sample cell, thereby detecting the reaction between, for example, a germ contained in milk and the antibody immobilized to the sample cell. However, the conventional SPR measuring device cannot detect whether a proper liquid sample flows on the sample cell. If an improper liquid sample flows, measurement fails.

The present invention has been made to solve the above problems, and has as its object to provide a surface plasmon resonance measuring device, sample cell, and measuring method capable of reducing the possibility that a measurement error occurs.

More specifically, it is an object of the present invention to easily and reliably identify a sample cell. It is another object of the present invention to determine whether the liquid sample is appropriate.

Means of Solution to the Problems

A surface plasmon resonance measuring device according to the present invention comprises a light source which irradiates, with condensed light, a sample cell having a characteristic structure of reflectance of light that is formed in advance as a code from at least one of a substance film to be measured and a substance film different from the substance film to be measured on part of a metal thin film, from a surface opposite to a surface on which the substance film to be measured is immobilized to the metal thin film, a camera which detects light reflected by the sample cell, and encoding means for extracting the code from a feature of an image sensed by the camera.

A sample cell for measuring surface plasmon resonance according to the present invention comprises a characteristic structure of reflectance of light that is formed in advance as a code from at least one of a substance film to be measured and a substance film different from the substance film to be measured on part of a metal thin film.

A surface plasmon resonance measuring method according to the present invention comprises the irradiation step of irradiating, with condensed light, a sample cell having a characteristic structure of reflectance of light that is formed in advance as a code from at least one of a substance film to be measured and a substance film different from the substance film to be measured on part of a metal thin film, from a surface opposite to a surface on which the substance film to be measured is immobilized to the metal thin film, the image sensing step of detecting light reflected by the sample cell, and the encoding step of extracting the code from a feature of an image sensed in the image sensing step.

Effects of the Invention

According to the present invention, a sample cell having the characteristic structure of the reflectance of light that is formed in advance as a code from at least either of a substance film to be measured and a substance film different from the substance film to be measured is irradiated with light. An image of the sample cell sensed by a camera is processed, extracting a code from the feature of the image. Based on the extracted code, the sample cell can be easily and reliably identified. Also based on the code, it can be determined whether the liquid sample is appropriate. The possibility that a measurement error occurs can therefore be reduced.

BEST MODE FOR CARRYING OUT THE INVENTION

First Embodiment

Figure 1:
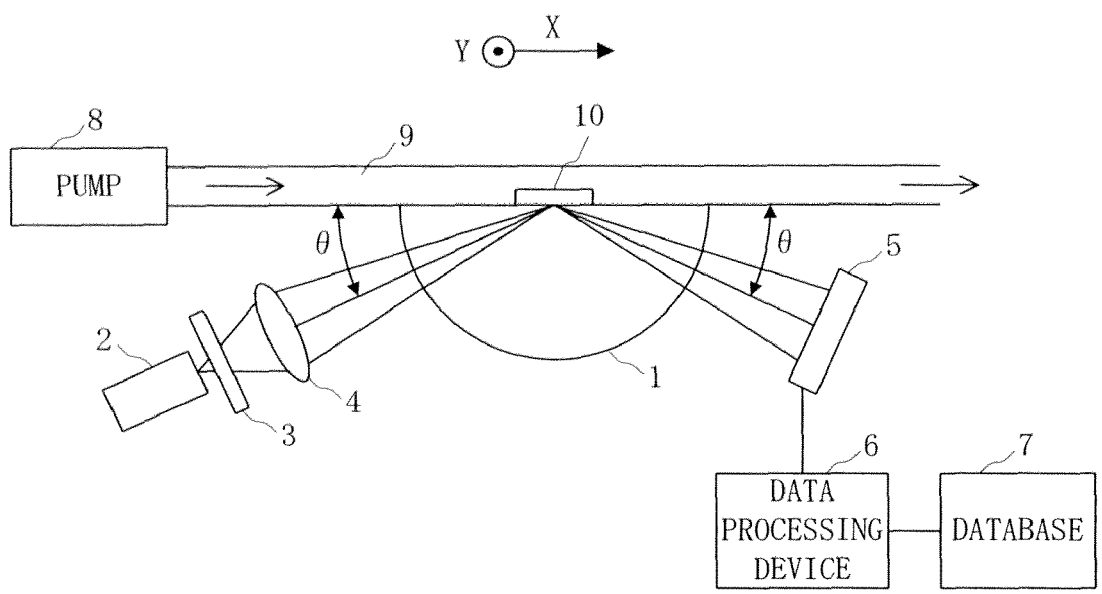
FIG. 1 is a block diagram showing the arrangement of a surface plasmon resonance measuring device according to the first embodiment of the present invention.

The first embodiment of the present invention will be described below with reference to the accompanying drawings. FIG. 1 is a block diagram showing the arrangement of an SPR measuring device according to the first embodiment of the present invention.

The SPR measuring device according to the first embodiment includes a prism 1, a light source 2, a polarizing plate 3, a condenser lens 4, a CCD camera 5, a data processing device 6, a database 7, a pump 8 for supplying a liquid sample to a sample cell 10, and a channel 9 through which the liquid sample flows.

Figure 2A:
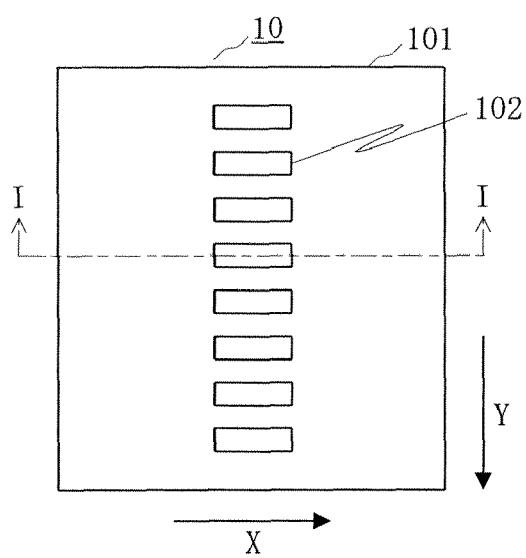
FIG. 2A is a plan view showing the general structure of a sample cell.
Figure 2B:
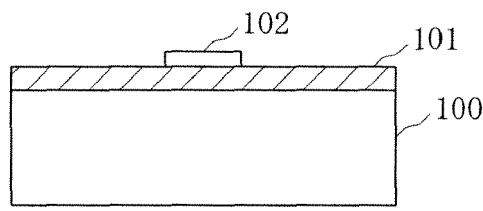
FIG. 2B is a sectional view of the sample cell in FIG. 2A.

FIG. 2A is a plan view showing the general structure of the sample cell 10. FIG. 2B is a sectional view of the sample cell 10 taken along a line I-I in FIG. 2A. In FIGS. 2A and 2B, a plate-like transparent body 100 is made of a material having the same refractive index as that of the prism 1. A metal thin film 101 is formed from gold or silver on the transparent body 100 by sputtering, vapor deposition, or the like and has a thickness of about 40 to 60 nm. Substance films 102 to be measured, such as an antibody, are immobilized on the metal thin film 101.

Figure 3:
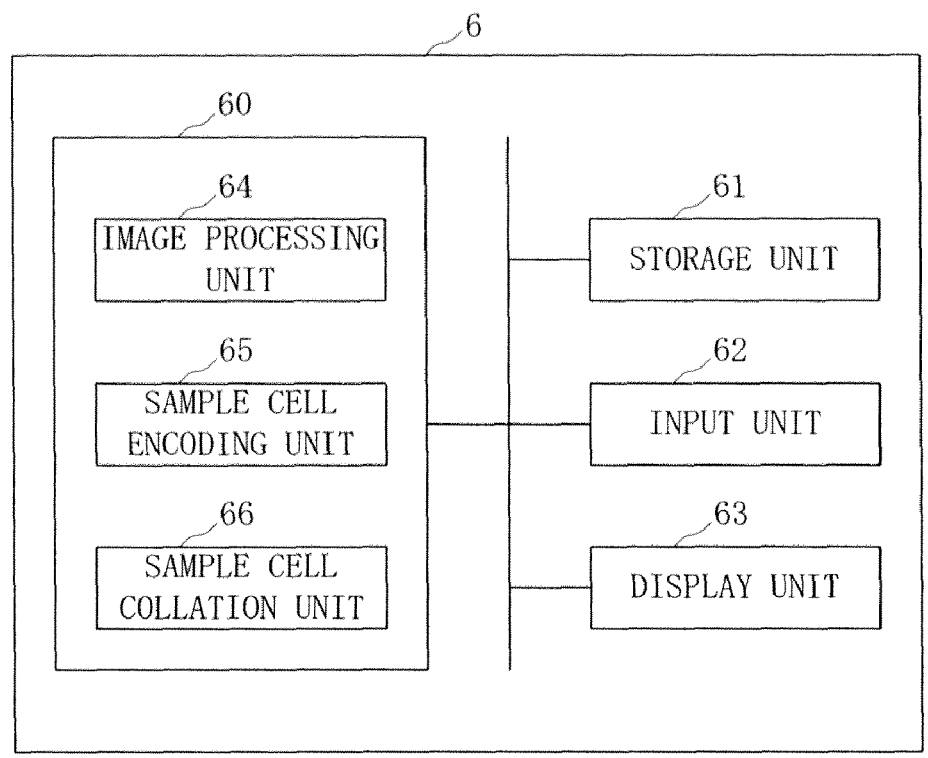
FIG. 3 is a block diagram exemplifying the arrangement of the data processing device of the surface plasmon resonance measuring device according to the first embodiment of the present invention.

FIG. 3 is a block diagram exemplifying the arrangement of the data processing device 6. The data processing device 6 includes a control unit 60 which controls the overall device, a storage unit 61 which stores programs and the like for the control unit 60, an input unit 62 for inputting an instruction from the user of the SPR measuring device to the device, and a display unit 63 which displays information for the user.

The control unit 60 includes an image processing unit 64, sample cell encoding unit 65, and sample cell collation unit 66.

Figure 4:
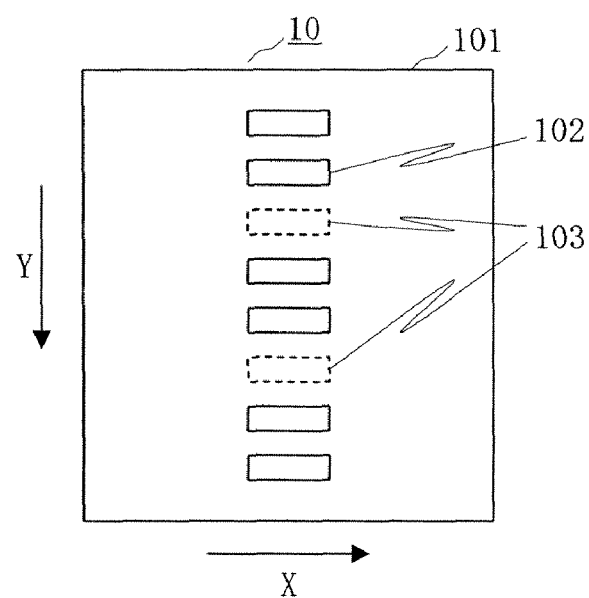
FIG. 4 is a plan view showing the structure of the sample cell used in the first embodiment of the present invention.
Figure 5:
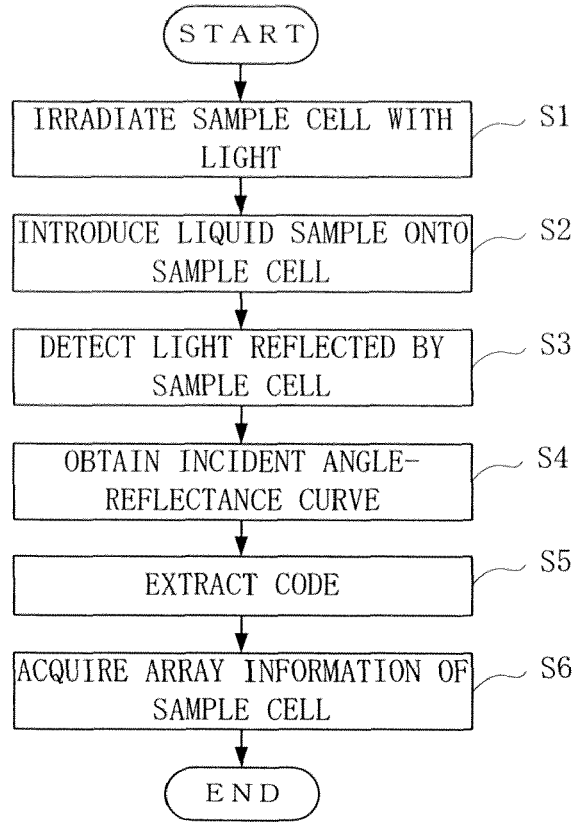
FIG. 5 is a flowchart showing the operation of the surface plasmon resonance measuring device according to the first embodiment of the present invention.

The operation of the SPR measuring device in the first embodiment will be explained. FIG. 4 is a plan view showing the structure of the sample cell 10 used in the first embodiment. FIG. 5 is a flowchart showing the operation of the SPR measuring device.

The first embodiment employs the sample cell 10 having the metal thin film 101 formed on the transparent body 100, the substance films 102 to be measured that are immobilized at substance-film-to-be measured arrangement portions on the metal thin film 101, and blank portions 103 having no substance film to be measured at a substance-film-to-be-measured arrangement portion. The sample cell 10 is set on the prism 1, with the substance films 102 to be measured facing up and the transparent body 100 in contact with the prism 1.

Similar to the conventional SPR measuring device, when light emitted by the light source 2 for monochromatic light reaches the polarizing plate 3, only p-polarized light passes. The p-polarized light is condensed by the condenser lens 4 and enters the prism 1. The p-polarized light enters the sample cell 10 from the transparent body 100 opposite to the surface on which the substance films 102 to be measured are immobilized (step S1 in FIG. 5).

When supplying a liquid sample such as milk, the pump 8 pumps the liquid sample. The liquid sample flows through the channel 9 and passes on the sample cell 10 (step S2).

The CCD camera 5 detects light reflected by the sample cell 10, outputting grayscale image data (step S3).

Figure 35:
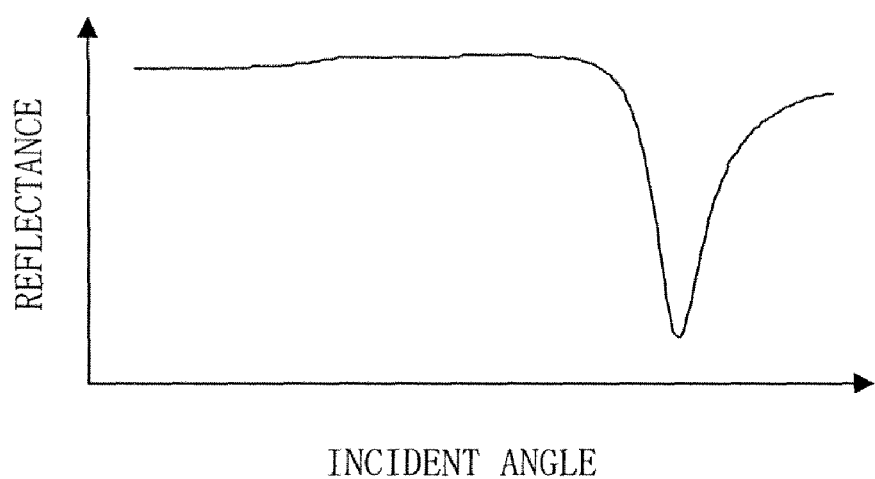
FIG. 35 is a graph exemplifying an incident angle-reflectance curve obtained by measuring a sample cell by the conventional surface plasmon resonance measuring device.

The image processing unit 64 of the data processing device 6 processes the grayscale image data output from the CCD camera 5, obtaining data of an incident angle-reflectance curve as shown in FIG. 35 for each substance film 102 to be measured on the sample cell 10 (step S4).

Figure 6:
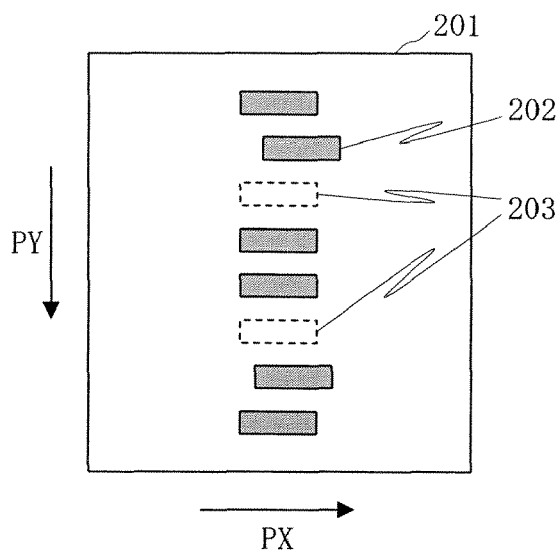
FIG. 6 is a view schematically showing an image sensed by a CCD camera in the first embodiment of the present invention.

FIG. 6 is a view schematically showing an image sensed by the CCD camera 5. The image sensed by the CCD camera 5 has a tone corresponding to the reflectance of light at each portion of the sample cell 10. In FIG. 6, a bright (high reflectance) region 201 corresponds to the metal thin film 101. A dark (low reflectance) region 202 exhibits a reflectance valley corresponding to the substance film 102 to be measured. In FIG. 6, a dotted line indicates a region 203 corresponding to the blank portion 103 (substance-film-to-be-measured arrangement portion).

The PX direction in FIG. 6 represents the incident angle θ in FIG. 1. The image processing unit 64 can convert the PX-coordinate of grayscale image data into the incident angle θ. In FIG. 6, some of the image regions 202 corresponding to reflectance valleys generated by the substance films 102 to be measured shift in PX-coordinate. This is because, for example, the refractive index changes upon reaction between a substance (antigen) in the liquid sample and the substance film 102 (antibody) to be measured, slightly changing the incident angle at which the evanescent wave and surface plasmon wave resonate with each other.

The brightness of the grayscale image in FIG. 6 changes depending on the reflectance of the sample cell 10. The image processing unit 64 can convert the intensity value of each pixel of the grayscale image data into the reflectance of light.

For each substance-film-to-be-measured arrangement portion, the image processing unit 64 derives an incident angle-reflectance curve at the PY-coordinate corresponding to the substance-film-to-be-measured arrangement portion. Data of the incident angle-reflectance curve can therefore be obtained for each substance film 102 to be measured. Note that the PY direction in FIG. 6 is equivalent to the Y direction perpendicular to the sheet surface of FIG. 1.

Figure 7:
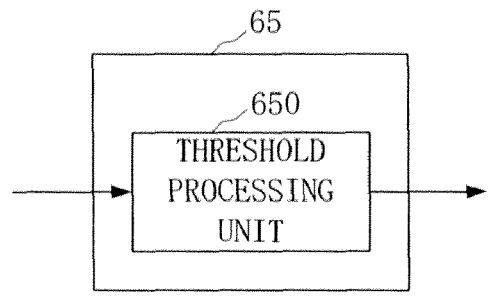
FIG. 7 is a block diagram exemplifying the arrangement of the sample cell encoding unit of the data processing device according to the first embodiment of the present invention.

After that, the sample cell encoding unit 65 of the data processing device 6 encodes the presence/absence of the substance film 102 to be measured on the sample cell 10, and identifies the sample cell 10 (step S5). FIG. 7 is a block diagram exemplifying the arrangement of the sample cell encoding unit 65. The sample cell encoding unit 65 includes a threshold processing unit 650.

In the grayscale image as shown in FIG. 6, the positions of substance-film-to-be-measured arrangement portions on the sample cell 10 are known. If the intensity value at a substance-film-to-be-measured arrangement portion in the grayscale image output from the CCD camera 5 is smaller than a predetermined threshold, the threshold processing unit 650 determines that a substance film to be measured exists, and sets, for example, a value "1". If the intensity value at a substance-film-to-be-measured arrangement portion is equal to or larger than the threshold, the threshold processing unit 650 determines that no substance film to be measured exists, and sets, for example, a value "0". The threshold processing unit 650 executes this encoding sequentially for respective substance-film-to-be-measured arrangement portions in the PY direction in FIG. 6.

In the example of FIG. 6, the first, second, fourth, fifth, seventh, and eighth substance-film-to-be-measured arrangement portions from the top are dark, and the third and sixth substance-film-to-be-measured arrangement portions from the top are bright. The image in FIG. 6 is encoded based on the presence/absence of a substance film to be measured in the PY direction, obtaining a code "11011011". In this fashion, the identification code of the sample cell 10 shown in FIG. 4 can be extracted.

In the database 7, the identification code of a sample cell, and array information of substance films to be measured on the sample cell are registered in advance in correspondence with each other. The array information includes information indicating the content of a substance film to be measured, and position information indicating the position where the substance film to be measured is arranged on the sample cell.

By referring to the database 7, the sample cell collation unit 66 of the data processing device 6 acquires, from the database 7, array information of a sample cell having an identification code coincident with the identification code output from the sample cell encoding unit 65. The display unit 63 displays the array information (step S6). According to the first embodiment, a sample cell can be identified in this way. The user of the SPR measuring device can recognize the content of a substance film to be measured and the position where the substance film to be measured is arranged on the sample cell.

Second Embodiment

The second embodiment of the present invention will be described. Also in the second embodiment, the arrangement and processing sequence of an SPR measuring device are the same as those in the first embodiment, and will be explained using the reference numerals in FIGS. 1, 3, and 5.

Figure 8A:
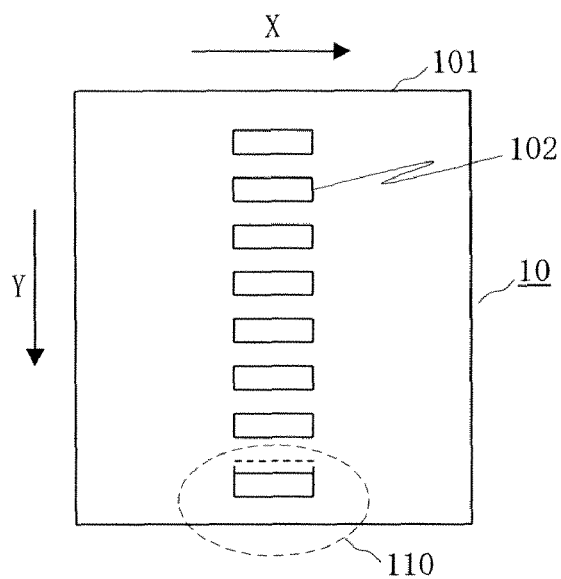
FIG. 8A is a plan view showing the structure of a sample cell used in the second embodiment of the present invention.
Figure 8B:
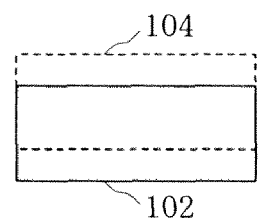
FIG. 8B is an enlarged view of the sample cell in FIG. 8A.

FIG. 8A is a plan view showing the structure of a sample cell 10 used in the second embodiment. FIG. 8B is an enlarged view of a portion 110 of the sample cell 10 in FIG. 8A.

Similar to the conventional SPR measuring device, substance films 102 to be measured are immobilized on a metal thin film 101. In the second embodiment, the Y position of at least one substance film 102 to be measured shifts from the position of a substance-film-to-be-measured arrangement portion 104, as shown in FIG. 80. A gap is set between adjacent substance films to be measured on the metal thin film 101. Thus, even if the substance film 102 to be measured slightly shifts from its original position in the Y direction, it does not affect measurement of the incident angle-reflectance curve. In the second embodiment, the position of the substance film 102 to be measured is shifted intentionally, and the shift amount is encoded to identify the sample cell 10.

Figure 9:
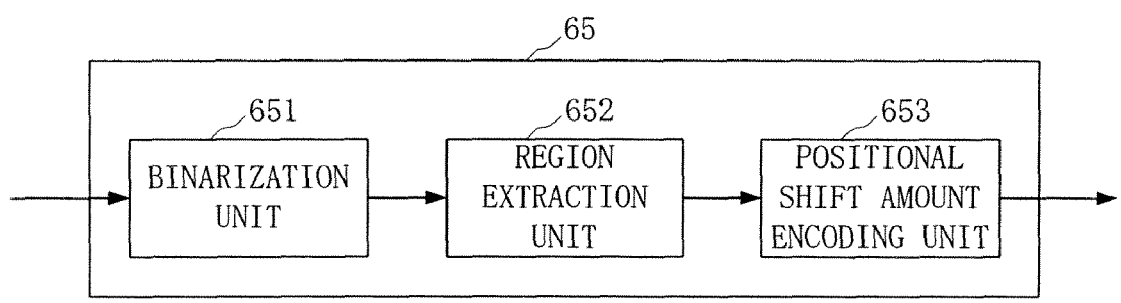
FIG. 9 is a block diagram exemplifying the arrangement of the sample cell encoding unit of a data processing device according to the second embodiment of the present invention.

FIG. 9 is a block diagram exemplifying the arrangement of a sample cell encoding unit 65 in the second embodiment. The sample cell encoding unit 65 includes a binarization unit 651, region extraction unit 652, and positional shift amount encoding unit 653.

Figure 10:
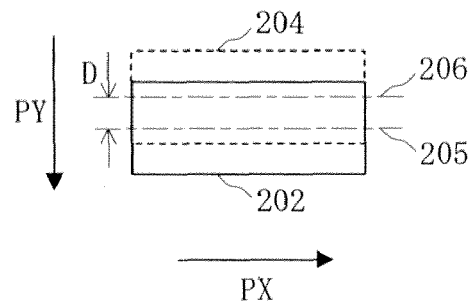
FIG. 10 is a view for explaining the operation of the sample cell encoding unit in the second embodiment of the present invention.

FIG. 10 is a view for explaining the operation of the sample cell encoding unit 65 in the second embodiment. In a grayscale image sensed by a CCD camera 5, an encoding portion 204 at which the substance film 102 to be measured is intentionally shifted is known. In the example of FIG. 8A, the substance film 102 to be measured at the final substance-film-to-be-measured arrangement portion 104 in the Y direction is used as an encoding target. In the grayscale image obtained by sensing the sample cell 10, a position corresponding to the substance-film-to-be-measured arrangement portion 104 is the encoding portion 204.

The binarization unit 651 of the sample cell encoding unit 65 binarizes grayscale image data output from the CCD camera 5 by using a predetermined threshold. From the binary image, the region extraction unit 652 extracts, as an image region 202 of the substance film 102 to be measured serving as an encoding target, a region darker than the threshold in a predetermined search range for the known encoding portion 204. The region extraction unit 652 obtains a center line 205 of the image region 202 (FIG. 10). The positional shift amount encoding unit 653 calculates a positional shift amount D of the center line 205 in the PY direction from a predetermined center line 206 of the encoding portion 204. The positional shift amount encoding unit 653 encodes the positional shift amount D. For example, four positional shift amounts D are defined, and values "0", "1", "2", and "3" are assigned in advance to the four positional shift amounts D. The positional shift amount D can be encoded at 2 bits.

Accordingly, the identification code of the sample cell 10 shown in FIG. 8A can be extracted. The same effects as those in the first embodiment can be obtained.

In the second embodiment, one of the substance films 102 to be measured on the metal thin film 101 is used as an encoding target. It is also possible to set a plurality of substance films 102 to be measured as encoding targets and shift their positions from the substance-film-to-be-measured arrangement portions 104. When n substance films 102 to be measured are set as encoding targets, a 4^n identification code can be assigned to the sample cell 10.

Third Embodiment

The positional shift amount of the substance film 102 to be measured is encoded in the second embodiment, but the width of the substance film 102 to be measured may be encoded. In the third embodiment, the Y width of at least one substance film 102 to be measured serving as an encoding target among a plurality of substance films 102 to be measured on a sample cell 10 is shifted intentionally from the original width, and the shifted width is encoded.

Figure 11:
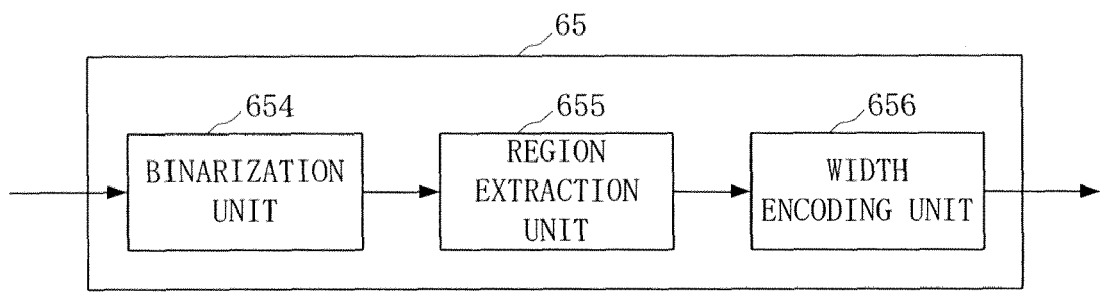
FIG. 11 is a block diagram exemplifying the arrangement of the sample cell encoding unit of a data processing device according to the third embodiment of the present invention.

FIG. 11 is a block diagram exemplifying the arrangement of a sample cell encoding unit 65 in the third embodiment. The sample cell encoding unit 65 includes a binarization unit 654, region extraction unit 655, and width encoding unit 656.

Figure 12:
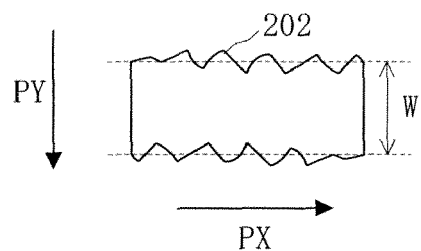
FIG. 12 is a view for explaining the operation of the sample cell encoding unit in the third embodiment of the present invention.

FIG. 12 is a view for explaining the operation of the sample cell encoding unit 65 in the third embodiment. The binarization unit 654 of the sample cell encoding unit 65 binarizes grayscale image data output from a CCD camera 5 by using a predetermined threshold. From the binary image, the region extraction unit 655 extracts, as an image region 202 of the substance film 102 to be measured serving as an encoding target, a region darker than the threshold in a predetermined search range for a known encoding portion 204. The region extraction unit 655 obtains the PY width W of the image region 202 (FIG. 12).

At this time, the edge of the actual region 202 is waved. Thus, the width encoding unit 656 calculates the average PY width of the image region 202, sets the average width as the width W, and encodes the width W. For example, four widths W are defined, and values "0", "1", "2", and "3" are assigned in advance to the four widths W. The width W can be encoded at 2 bits.

According to the third embodiment, the identification code of the sample cell 10 can be extracted. The same effects as those in the first embodiment can be obtained.

Similar to the second embodiment, a plurality of substance films 102 to be measured on a metal thin film 101 may be set as encoding targets.

Fourth Embodiment

The width of the substance film 102 to be measured is encoded in the third embodiment, but the start and end positions of the substance film 102 to be measured may be encoded. In the fourth embodiment, the Y start and end positions of at least one substance film 102 to be measured serving as an encoding target among a plurality of substance films 102 to be measured on a sample cell 10 are shifted intentionally from the original positions, and the shifted start and end positions are encoded.

Figure 13:
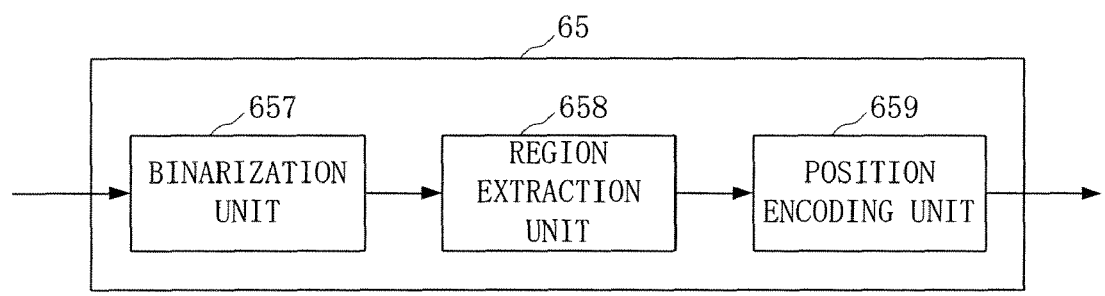
FIG. 13 is a block diagram exemplifying the arrangement of the sample cell encoding unit of a data processing device according to the fourth embodiment of the present invention.

FIG. 13 is a block diagram exemplifying the arrangement of a sample cell encoding unit 65 in the fourth embodiment. The sample cell encoding unit 65 includes a binarization unit 657, region extraction unit 658, and position encoding unit 659.

Figure 14:
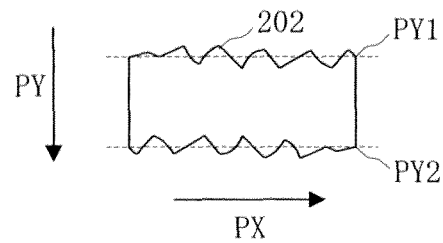
FIG. 14 is a view for explaining the operation of the sample cell encoding unit in the fourth embodiment of the present invention.

FIG. 14 is a view for explaining the operation of the sample cell encoding unit 65 in the fourth embodiment. The binarization unit 657 of the sample cell encoding unit 65 binarizes grayscale image data output from a CCD camera 5 by using a predetermined threshold. From the binary image, the region extraction unit 658 extracts, as an image region 202 of the substance film 102 to be measured serving as an encoding target, a region darker than the threshold in a predetermined search range for a known encoding portion. The region extraction unit 658 obtains a PY start position PY1 and end position PY2 of the image region 202 (FIG. 14).

As described in the third embodiment, the edge of the region 202 is waved. Thus, the position encoding unit 659 sets the average value of the PY start position of the image region 202 as the start position PY1, and the average value of the PY end position of the image region 202 as the end position PY2. The position encoding unit 659 encodes the start position PY1 and end position PY2. The position may be encoded by assigning different values to respective start positions PY1. The position may be encoded by assigning different values to respective end positions PY2. Alternatively, the position may be encoded by assigning different values to respective combinations of the start position PY1 and end position PY2.

According to the fourth embodiment, the identification code of the sample cell 10 can be extracted. The same effects as those in the first embodiment can be obtained. Similar to the second embodiment, a plurality of substance films 102 to be measured on a metal thin film 101 may be set as encoding targets.

Fifth Embodiment

Figure 15:
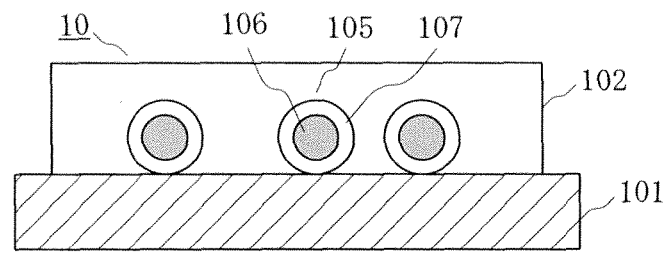
FIG. 15 is a sectional view showing the structure of a sample cell used in the fifth embodiment of the present invention.

The fifth embodiment of the present invention will be described. FIG. 15 is a sectional view showing the structure of a sample cell 10 used in the fifth embodiment. Similar to the conventional SPR measuring device, substance films 102 to be measured are immobilized on a metal thin film 101. In the fifth embodiment, property control members 105 different in imaginary part of the refractive index from the substance film 102 to be measured are buried in the substance film 102 to be measured. With this structure, the minimum reflectance of the incident angle-reflectance curve is intentionally shifted. The shifted minimum reflectance is encoded to identify the sample cell 10.

The property control member 105 is obtained by covering, with an outer coat 107 made of a low refractive index material such as porous glass, a bead 106 which is made of a high refractive index material such as latex or polystyrene and has a nm-size diameter.

Figure 16:
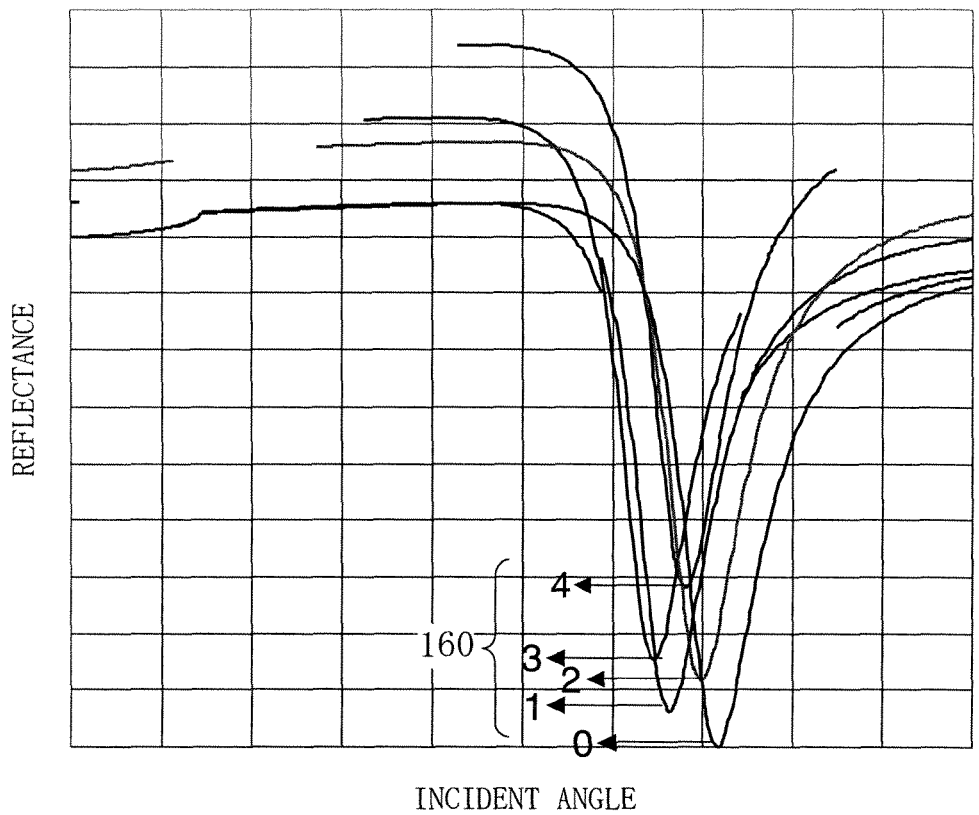
FIG. 16 is a graph exemplifying a change of an incident angle-reflectance curve obtained by measuring the sample cell in the fifth embodiment of the present invention.

By changing the concentration of the property control members 105 in the substance film 102 to be measured, the minimum reflectance of the incident angle-reflectance curve can be shifted intentionally, as shown in FIG. 16. By assigning different values to respective minimum reflectances, the minimum reflectance can be encoded. In the example of FIG. 16, values "0", "1", "2", "3", and "4" are attained as examples of a code 160 in accordance with five minimum reflectances.

Figure 17:
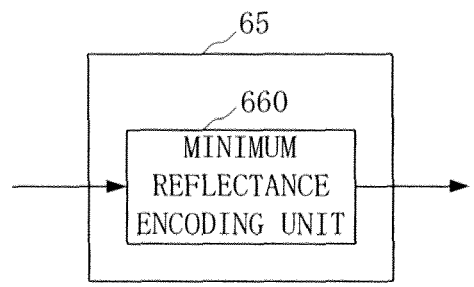
FIG. 17 is a block diagram exemplifying the arrangement of the sample cell encoding unit of a data processing device according to the fifth embodiment of the present invention.

In the fifth embodiment, an image processing unit 64 constitutes an encoding means together with a sample cell encoding unit 65. FIG. 17 is a block diagram exemplifying the arrangement of the sample cell encoding unit 65 in the fifth embodiment. The sample cell encoding unit 65 includes a minimum reflectance encoding unit 660.

The minimum reflectance encoding unit 660 obtains a minimum reflectance from data of an incident angle-reflectance curve of the substance film 102 to be measured serving as an encoding target (substance film 102 to be measured containing the property control members 105) at a known encoding portion, out of data of incident angle-reflectance curves attained by the image processing unit 64 for the respective substance films 102 to be measured on the sample cell 10. The minimum reflectance encoding unit 660 encodes the minimum reflectance by converting it into a value assigned in advance.

According to the fifth embodiment, the identification code of the sample cell 10 can be extracted. The same effects as those in the first embodiment can be obtained. Similar to the second embodiment, a plurality of substance films 102 to be measured on the metal thin film 101 may be set as encoding targets.

Sixth Embodiment

Figure 18:
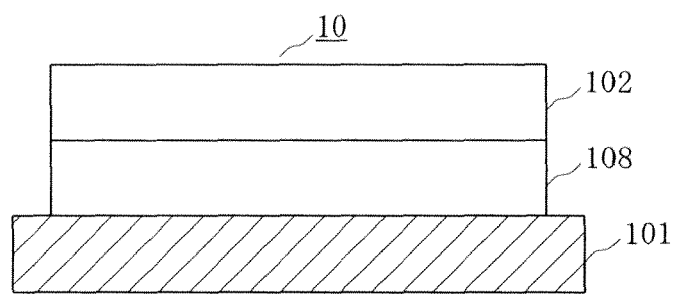
FIG. 18 is a sectional view showing the structure of a sample cell used in the sixth embodiment of the present invention.
Figure 19:
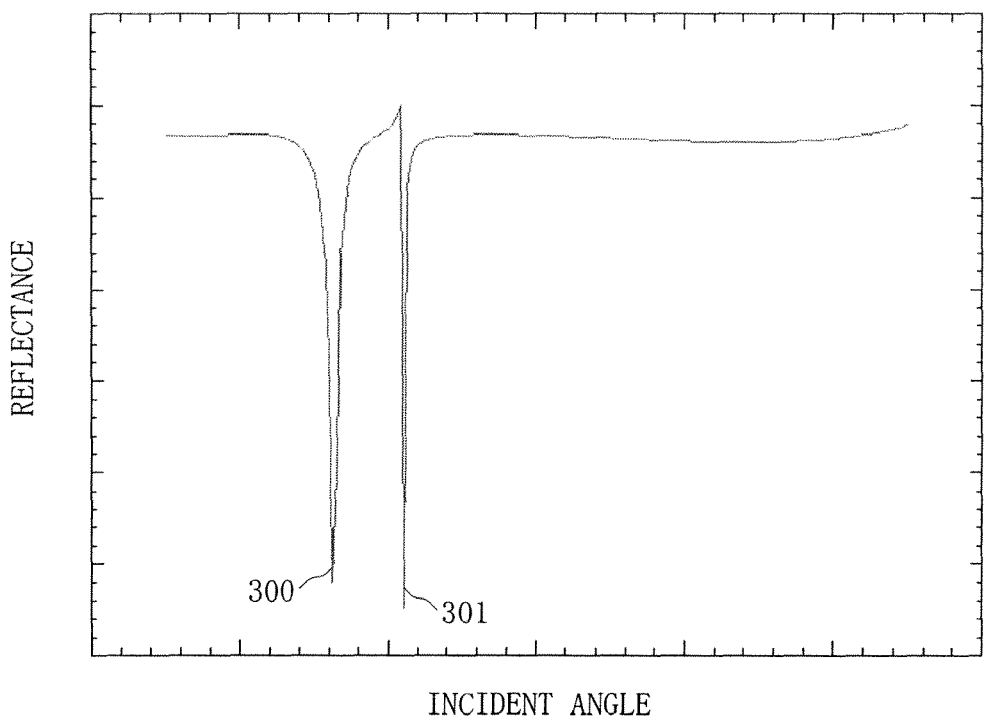
FIG. 19 is a graph exemplifying an incident angle-reflectance curve obtained by measuring the sample cell in the sixth embodiment of the present invention.

The sixth embodiment of the present invention will be described. FIG. 18 is a sectional view showing the structure of a sample cell 10 used in the sixth embodiment. In the sixth embodiment, a property control layer 108 made of a material lower in refractive index than a substance film 102 to be measured is sandwiched between a metal thin film 101 and the substance film 102 to be measured. The property control layer 108 generates a reflectance valley 301 in the incident angle-reflectance curve in addition to an original reflectance valley 300, as shown in FIG. 19. The presence/absence of the reflectance valley 301 is encoded to identify the sample cell 10.

Figure 20:
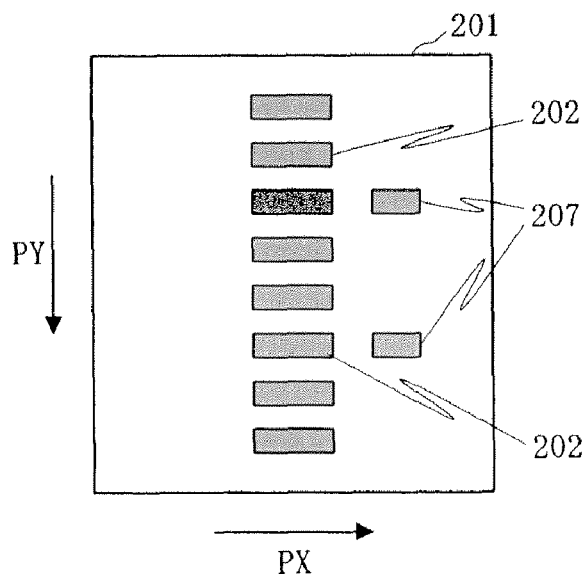
FIG. 20 is a view schematically showing an image sensed by a CCD camera in the sixth embodiment of the present invention.

FIG. 20 is a view schematically showing an image sensed by a CCD camera 5 in the sixth embodiment. Assume that the property control layers 108 are formed in the third and sixth substance films 102 to be measured in the Y direction. In the image sensed by the CCD camera 5, image regions 207 indicating the reflectance valley 301 appear at the third and sixth portions in the PY direction, in addition to dark image regions 202 indicating the original reflectance valley 300, as shown in FIG. 20.

Figure 21:
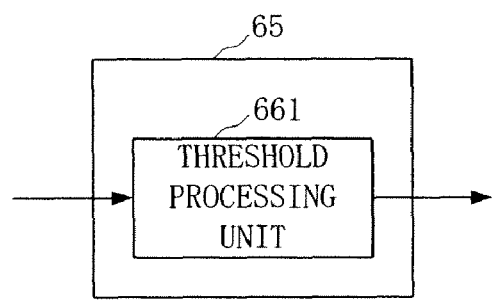
FIG. 21 is a block diagram exemplifying the arrangement of the sample cell encoding unit of a data processing device according to the sixth embodiment of the present invention.

FIG. 21 is a block diagram exemplifying the arrangement of a sample cell encoding unit 65 in the sixth embodiment. The sample cell encoding unit 65 includes a threshold processing unit 661.

As described in the first embodiment, the positions of substance-film-to-be-measured arrangement portions on the sample cell 10 are known in a grayscale image sensed by the CCD camera 5. If a portion 1 we in intensity value than a predetermined threshold exists at the same PY coordinate as that of a substance-film-to-be-measured arrangement portion in the grayscale image output from the CCD camera 5, the threshold processing unit 661 sets, for example, a value "1". If two portions lower in intensity value than the predetermined threshold exist at the same PY coordinate as that of a substance-film-to-be-measured arrangement portion, the threshold processing unit 661 sets, for example, a value "0". The threshold processing unit 661 performs this encoding sequentially for respective substance-film-to-be-measured arrangement portions in the PY direction in FIG. 20.

The image in FIG. 20 is encoded based on the presence/absence of a substance film to be measured in the PY direction, obtaining a code "11011011".

According to the sixth embodiment, the identification code of the sample cell 10 can be extracted. The same effects as those in the first embodiment can be attained.

Seventh Embodiment

Figure 22:
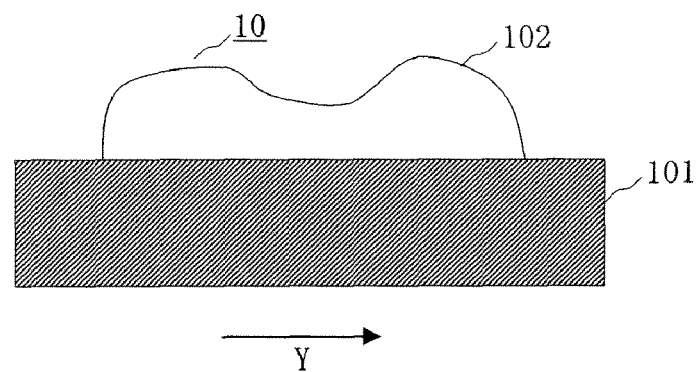
FIG. 22 is a sectional view showing the structure of a sample cell used in the seventh embodiment of the present invention.

The seventh embodiment of the present invention will be described. FIG. 22 is a sectional view showing the structure of a sample cell 10 used in the seventh embodiment. In the seventh embodiment, the film thickness of a substance film 102 to be measured that is immobilized on a metal thin film 101 is changed in the Y direction within the single substance film 102 to be measured, thereby forming a shape (refractive index distribution) in the PY direction in an image region 202. The sample cell 10 is identified by determining whether the shape contains a valley or hill, or assigning codes to a valley and hill.

The film thickness pattern of the substance film 102 to be measured can be formed by changing the glycerin concentration of the solution of the substance film 102 to be measured and controlling the evaporation rate. The film thickness may be changed by applying the substance film 102 to be measured by a plurality of number of times.

Figure 23:
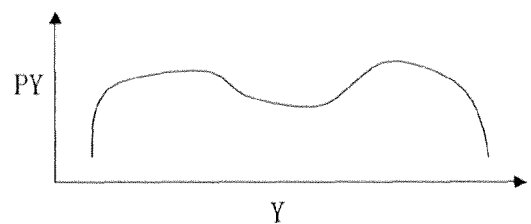
FIG. 23 is a graph exemplifying a refractive index distribution curve obtained by measuring the sample cell in the seventh embodiment of the present invention.

When the sample cell 10 as shown in FIG. 22 is measured, the PY value draws a curve corresponding to the film thickness pattern of the substance film 102 to be measured in the Y direction, as shown in FIG. 23. More specifically, the PY value is large at a portion where the substance film 102 to be measured is thick, and small at a portion where it is thin.

Figure 24:
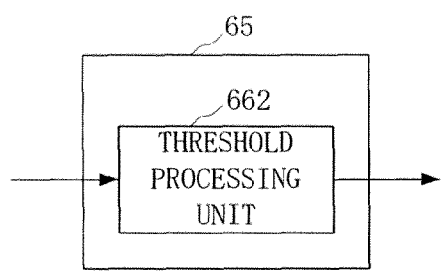
FIG. 24 is a block diagram exemplifying the arrangement of the sample cell encoding unit of a data processing device according to the seventh embodiment of the present invention.

FIG. 24 is a block diagram exemplifying the arrangement of a sample cell encoding unit 65 in the seventh embodiment. The sample cell encoding unit 65 includes a threshold processing unit 662.

If a portion lower in intensity value than a predetermined threshold exists at the same PY coordinate as that of a substance-film-to-be-measured arrangement portion in a grayscale image output from a CCD camera 5, the threshold processing unit 662 sets, for example, a value "1". If a plurality of portions lower in intensity value than the predetermined threshold exist at the same PY coordinate as that of a substance-film-to-be-measured arrangement portion, the threshold processing unit 662 sets, for example, a value "0". This threshold needs to be set to a value at which a change of the refractive index caused by a change of the film thickness of one substance film 102 to be measured can be detected. The threshold processing unit 662 executes this encoding sequentially for respective substance-film-to-be-measured arrangement portions in the PY direction.

According to the seventh embodiment, the identification code of the sample cell 10 can be extracted. The same effects as those in the first embodiment can be attained. Similar to the second embodiment, a plurality of substance films 102 to be measured on the metal thin film 101 may be set as encoding targets.

Eighth Embodiment

Figure 25:
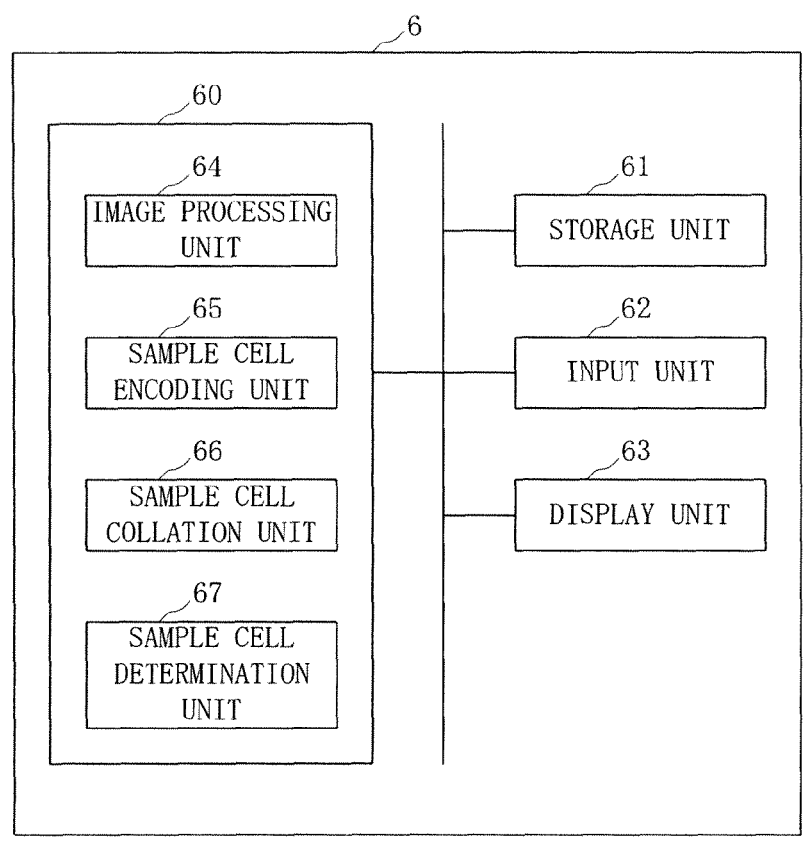
FIG. 25 is a block diagram exemplifying the arrangement of the data processing device of a surface plasmon resonance measuring device according to the eighth embodiment of the present invention.

The eighth embodiment of the present invention will be described. FIG. 25 is a block diagram exemplifying the arrangement of the data processing device of an SPR measuring device according to the eighth embodiment of the present invention.

A data processing device 6 in the eighth embodiment includes a control unit 60, storage unit 61, input unit 62, and display unit 63, similar to the first to seventh embodiments. Further, a sample cell determination unit 67 is added to the control unit 60.

Figure 26:
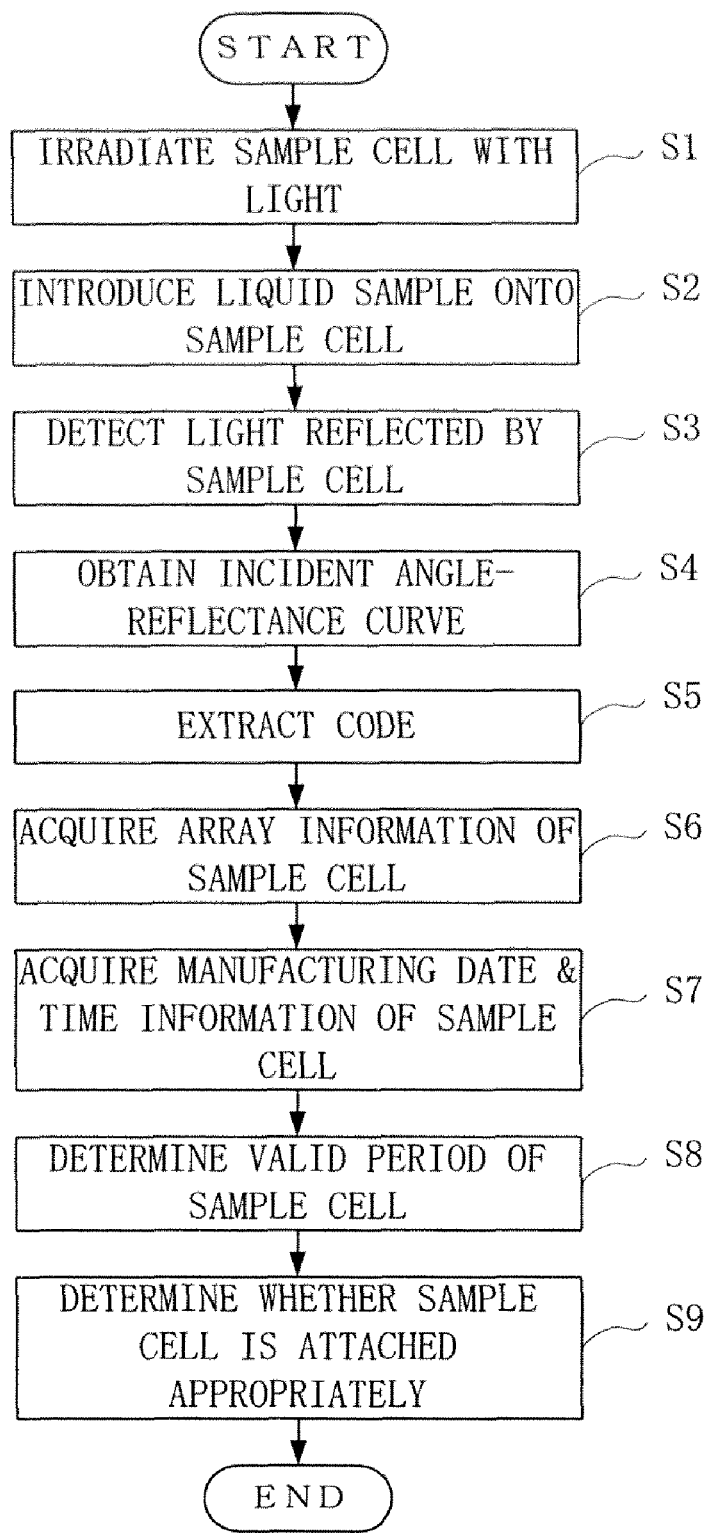
FIG. 26 is a flowchart showing the operation of the surface plasmon resonance measuring device according to the eighth embodiment of the present invention.

FIG. 26 is a flowchart showing the operation of the SPR measuring device in the eighth embodiment. The same reference numerals as those in FIG. 5 denote the same processes.

In the eighth embodiment, the identification code of a sample cell, and manufacturing date & time information of the sample cell are registered in advance in a database 7 in correspondence with each other.

By referring to the database 7, the sample cell determination unit 67 acquires, from the database 7, manufacturing date & time information of a sample cell having an identification code coincident with an identification code output from a sample cell encoding unit 65. The display unit 63 displays the manufacturing date & time information (step S7 in FIG. 26). Based on the acquired manufacturing date & time information, the sample cell determination unit 67 determines whether the valid period of the sample cell has not expired. The display unit 63 displays the determination result (step S8).

Based on an identification code output from the sample cell encoding unit 65, the sample cell determination unit 67 determines whether the attaching position and orientation of the sample cell are correct. The display unit 63 displays the determination result (step S9). For example, when the sample cell described in the first to seventh embodiments is measured and the identification code of this sample cell is not registered in the database 7 as a result of referring to the database 7, it can be determined that the attaching position or orientation of the sample cell with respect to a prism 1 is incorrect.

In the eighth embodiment, whether the valid period of the sample cell has expired or its attaching position is correct can be determined based on the identification code of the sample cell identified in the first to seventh embodiments. The user of the SPR measuring device can check whether the valid period of the sample cell has expired and also check whether the sample cell is attached appropriately.

The control unit 60 may include a means for correcting the activity of an antibody in accordance with manufacturing date & time information of a sample cell when measuring the concentration of an antigen based on the reaction between the antigen and the antibody. A change of the activity of the antibody with respect to days and time elapsed from the manufacturing date and time of a sample cell is measured in advance. Data of the elapsed days & time-activity curve is registered in the database 7 in advance. The activity of the antibody can be corrected based on days and time elapsed from the manufacturing date and time.

Ninth Embodiment

The ninth embodiment of the present invention will be explained. Similar to the first embodiment, an SPR measuring device includes a prism 1, light source 2, polarizing plate 3, condenser lens 4, CCD camera 5, data processing device 6, database 7, pump 8, and channel 9.

Figure 27:
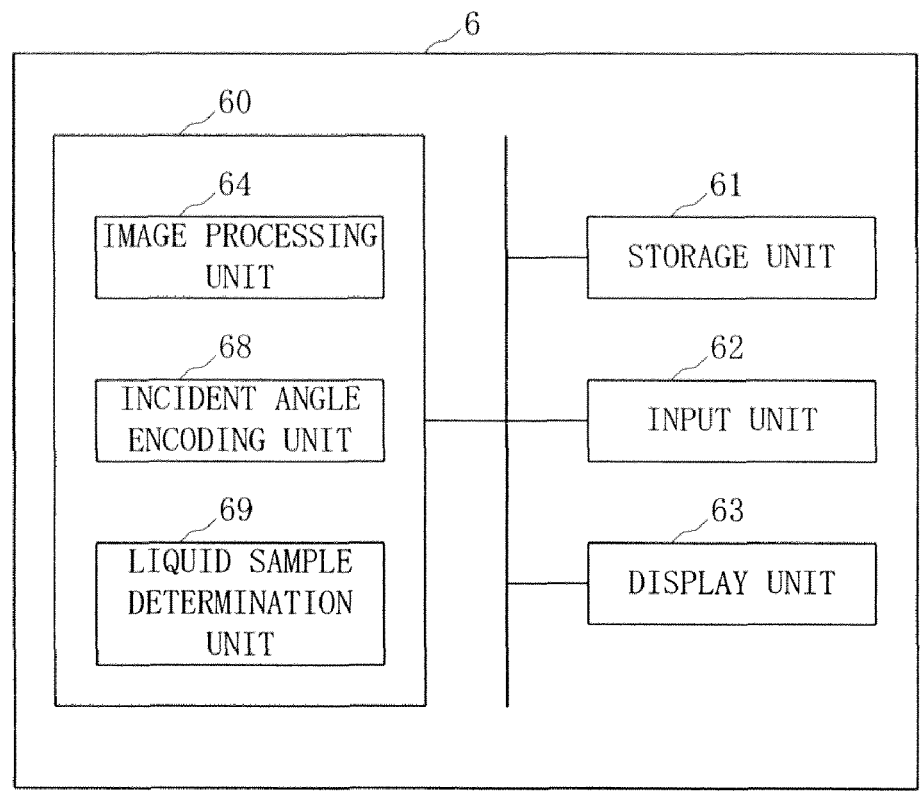
FIG. 27 is a block diagram exemplifying the arrangement of the data processing device of a surface plasmon resonance measuring device according to the ninth embodiment of the present invention.

FIG. 27 is a block diagram exemplifying the arrangement of the data processing device 6 in the ninth embodiment. The data processing device 6 includes a control unit 60 which controls the overall device, a storage unit 61 which stores programs and the like for the control unit 60, an input unit 62 for inputting an instruction from the user of the SPR measuring device to the device, and a display unit 63 which displays information for the user.

The control unit 60 includes an image processing unit 64, incident angle encoding unit 68, and liquid sample determination unit 69.

Figure 28:
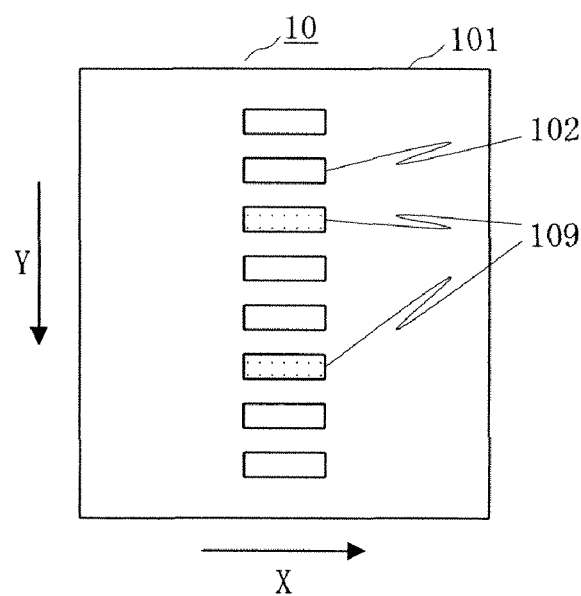
FIG. 28 is a plan view showing the structure of a sample cell used in the ninth embodiment of the present invention.
Figure 29:
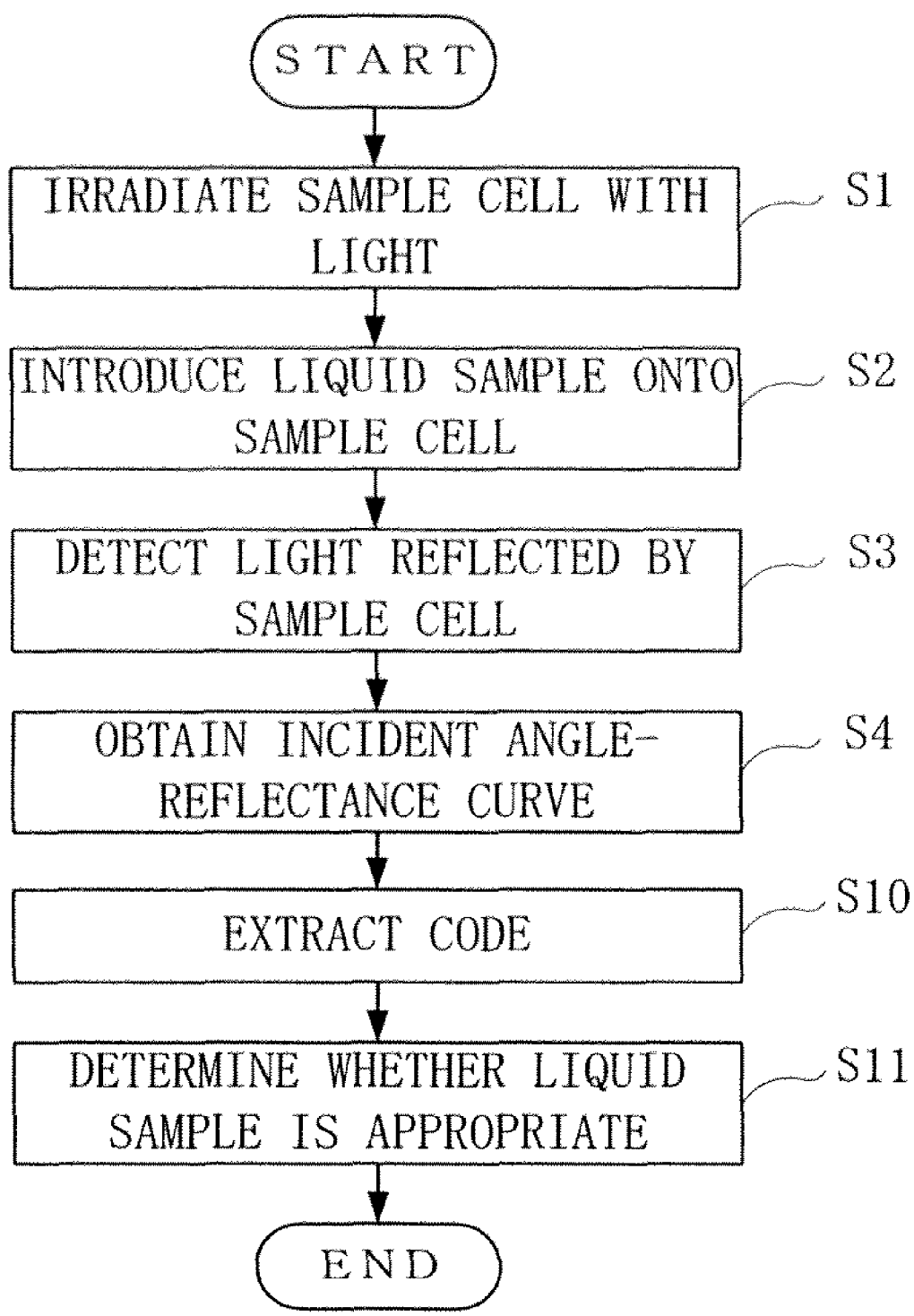
FIG. 29 is a flowchart showing the operation of the surface plasmon resonance measuring device according to the ninth embodiment of the present invention.

The operation of the SPR measuring device in the ninth embodiment will be explained. FIG. 28 is a plan view showing the structure of a sample cell 10 used in the ninth embodiment. FIG. 29 is a flowchart showing the operation of the SPR measuring device.

The ninth embodiment employs the sample cell 10 having a metal thin film 101 formed on a transparent body 100, substance films 102 to be measured that are immobilized at substance-film-to-be-measured arrangement portions on the metal thin film 101, and liquid sample detection substance films 109 that are immobilized at detection substance film arrangement portions on the metal thin film 101 and change in refractive index depending on the property of a liquid sample. Conceivable examples of the liquid sample detection substance film 109 are a substance film which is reduced upon reaction with a liquid sample, a substance film which disappears upon reaction with a liquid sample, and a substance film whose refractive index changes upon reaction with a liquid sample.

When the liquid sample is an aqueous solution, examples of the liquid sample detection substance film 109 are a salt which is highly soluble in water, such as sodium chloride or phosphate, and other water-soluble substance films. When the liquid sample is milk, examples of the liquid sample detection substance film 109 are antibodies to proteins which always exist in milk at high concentrations, such as anti-casein, anti-BSA, and when milk is foremilk, anti-Bovine IgG. When the liquid sample is blood, examples of the liquid sample detection substance film 109 are antibodies to proteins which always exist in blood at high concentrations, such as anti-albumin. The sample cell 10 is set on the prism 1, with the substance films 102 to be measured and the liquid sample detection substance films 109 facing up and the transparent body 100 in contact with the prism 1.

Similar to the first embodiment, when light emitted by the light source 2 for monochromatic light reaches the polarizing plate 3, only p-polarized light passes in the SPR measuring device shown in FIG. 1. The p-polarized light is condensed by the condenser lens 4 and enters the prism 1. The p-polarized light enters the sample cell 10 from the transparent body 100 opposite to the surface on which the substance films 102 to be measured are immobilized (step S1 in FIG. 29).

When supplying a liquid sample such as milk, the pump 8 pumps the liquid sample. The liquid sample flows through the channel 9 and passes on the sample cell 10 (step S2).

The CCD camera 5 detects light reflected by the sample cell 10, outputting grayscale image data (step S3).

The image processing unit 64 of the data processing device 6 processes the grayscale image data output from the CCD camera 5, obtaining data of an incident angle-reflectance curve as shown in FIG. 35 for each substance film 102 to be measured on the sample cell 10 (step S4).

Figure 30A:
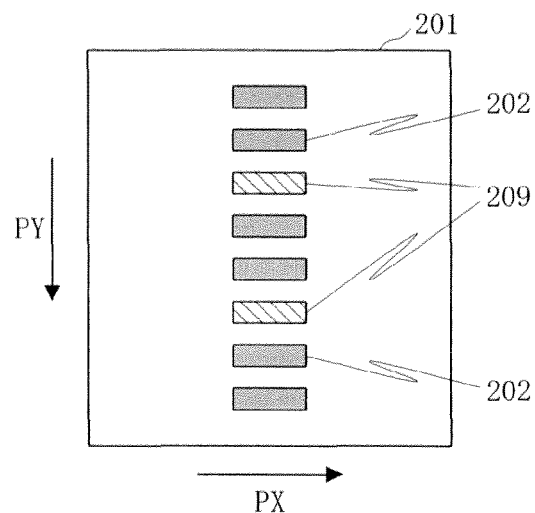
FIG. 30A is a view schematically showing an image sensed by a CCD camera before supplying a liquid sample in the ninth embodiment of the present invention.
Figure 30B:
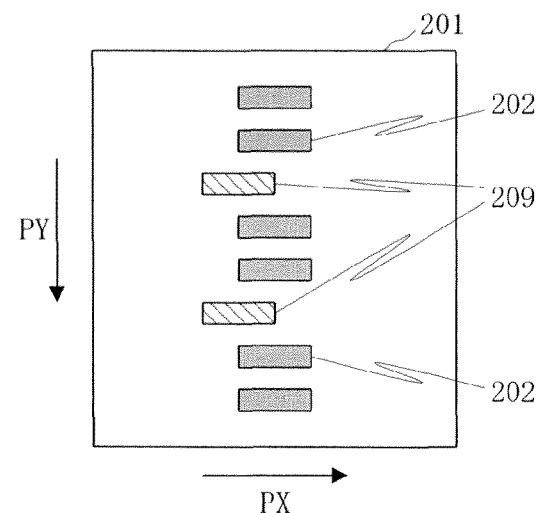
FIG. 30B is a view schematically showing an image sensed by a CCD camera 5 after supplying a liquid sample in the ninth embodiment of the present invention.

FIGS. 30A and 30B are views each schematically showing an image sensed by the CCD camera 5. FIG. 30A is a view showing an image sensed by the CCD camera 5 before supplying a liquid sample. FIG. 30B is a view showing an image sensed by the CCD camera 5 after supplying a liquid sample.

The image sensed by the CCD camera 5 has a tone corresponding to the reflectance of light at each portion of the sample cell 10. In FIGS. 30A and 30B, a bright (high reflectance) region 201 corresponds to the metal thin film 101. A dark (low reflectance) region 202 exhibits a reflectance valley corresponding to the substance film 102 to be measured. A dark (low reflectance) region 209 exhibits a reflectance valley corresponding to the liquid sample detection substance film 109.

The PX direction in FIGS. 30A and 30B is equivalent to the X direction in FIG. 1, and indicates the incident angle θ of light. The image processing unit 64 can convert the PX-coordinate of grayscale image data into the incident angle θ. In this case, the incident angle θ is given by the angle of light not with respect to a normal to the metal thin film 101 but with respect to the surface of the metal thin film 101. The brightness of the grayscale image in FIGS. 30A and 30B changes depending on the reflectance of the sample cell 10. The image processing unit 64 can convert the intensity value of each pixel of the grayscale image data into the reflectance of light. In the grayscale image sensed by the CCD camera 5, the positions of substance-film-to-be-measured arrangement portions and those of detection substance film arrangement portions on the sample cell 10 are known.

For each substance-film-to-be-measured arrangement portion, the image processing unit 64 derives an incident angle-reflectance curve at the PY-coordinate corresponding to the substance-film-to-be-measured arrangement portion. Data of the incident angle-reflectance curve can be obtained for each substance film 102 to be measured. Similarly, for each detection substance film arrangement portion, the image processing unit 64 derives an incident angle-reflectance curve at the PY-coordinate corresponding to the detection substance film arrangement portion. Data can be obtained for each liquid sample detection substance film 109. Note that the PY direction in FIGS. 30A and 30B is equivalent to the Y direction perpendicular to the sheet surface of FIG. 1.

The incident angle encoding unit 68 of the data processing device 6 obtains an incident angle at which the minimum reflectance is attained from the incident angle-reflectance curve measured by the image processing unit 64. Then, the incident angle encoding unit 68 encodes the incident angle (step S10).

For example, when an antigen in the liquid sample reacts with an antibody in the substance film 102 to be measured, the incident angle at which the reflectance valley appears changes. The incident angle-reflectance curve of the substance film 102 to be measured changes from characteristic A to characteristic B in FIG. 31.

Figure 31:
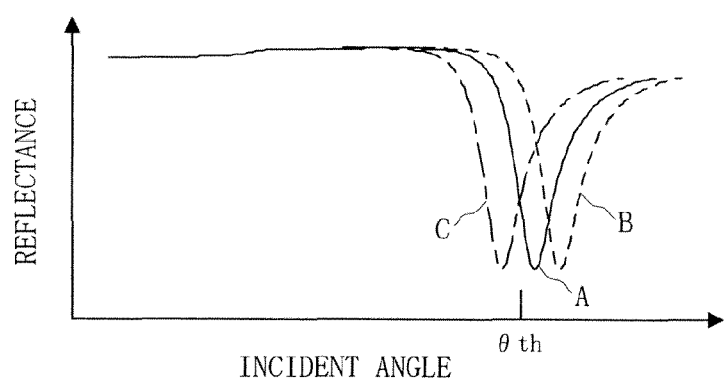
FIG. 31 is a graph showing a change of an incident angle-reflectance curve after introducing a liquid sample in the ninth embodiment of the present invention.

In contrast, when the liquid sample reacts with the liquid sample detection substance film 109 and the liquid sample detection substance film 109 is reduced or disappears, the incident angle-reflectance curve of the liquid sample detection substance film 109 changes from characteristic A to characteristic C in FIG. 31.

For example, by setting the threshold θth in FIG. 31, the reaction between a normal liquid sample and the liquid sample detection substance film 109 can be distinguished from no reaction of the liquid sample detection substance film 109 upon supplying an abnormal liquid sample.

The incident angle encoding unit 68 obtains, from the incident angle-reflectance curve measured by the image processing unit 64, an incident angle at which the minimum reflectance is attained. If the incident angle is larger than the threshold θth, the incident angle encoding unit 68 sets, for example, a value "1". If the incident angle is equal to or smaller than the threshold θth, the incident angle encoding unit 68 sets, for example, a value "0". The incident angle encoding unit 68 executes this encoding sequentially for respective substance-film-to-be-measured arrangement portions and respective detection substance film arrangement portions in the PY direction in FIGS. 30A and 30B.

In the example of FIG. 30A, no liquid sample has been introduced, so neither the substance film 102 to be measured nor liquid sample detection substance film 109 reacts. In this state, all incident angles at which the minimum reflectance is attained are larger than the threshold θth. These incident angles are encoded sequentially in the PY direction, obtaining a code "11111111".

In the example of FIG. 30B, a normal liquid sample is introduced, and the reflectance valley in an incident angle-reflectance curve obtained at a PY coordinate corresponding to a detection substance film arrangement portion shifts in a direction (leftward in FIG. 30B) in which the incident angle decreases. The incident angle at which the minimum reflectance is attained becomes equal to or smaller than the threshold θth. In the example of the sample cell 10 shown in FIG. 28, the third and sixth portions in the Y direction are detection substance film arrangement portions where the liquid sample detection substance films 109 are immobilized. Incident angles at which the reflectance is attained in the image in FIG. 30B obtained by sensing the sample cell 10 after introducing a liquid sample are encoded sequentially in the PY direction, obtaining a code "11011011".

In the database 7, incident angle codes upon reaction with a normal liquid sample are registered in advance.

The liquid sample determination unit 69 determines whether the liquid sample is appropriate, based on a code output from the incident angle encoding unit 68 after supplying the liquid sample (step S11). More specifically, if a code output from the incident angle encoding unit 68 is registered in the database 7, the liquid sample determination unit 69 determines that a normal liquid sample has been supplied. If a code output from the incident angle encoding unit 68 is not registered in the database 7, the liquid sample determination unit 69 determines that the liquid sample is not appropriate. The liquid sample determination unit 69 displays the determination result on the display unit 63. According to the ninth embodiment, whether the liquid sample is appropriate can be determined in this fashion.

10th Embodiment

The 10th embodiment of the present invention will be described. The 10th embodiment is directed to a combination of the sample cell identification technique described in the first to eighth embodiments and the liquid sample appropriateness determination technique described in the ninth embodiment. Also in the 10th embodiment, an SPR measuring device includes a prism light source 2, polarizing plate 3, condenser lens 4, CCD camera 5, data processing device 6, database 7, pump 8, and channel 9.

Figure 32:
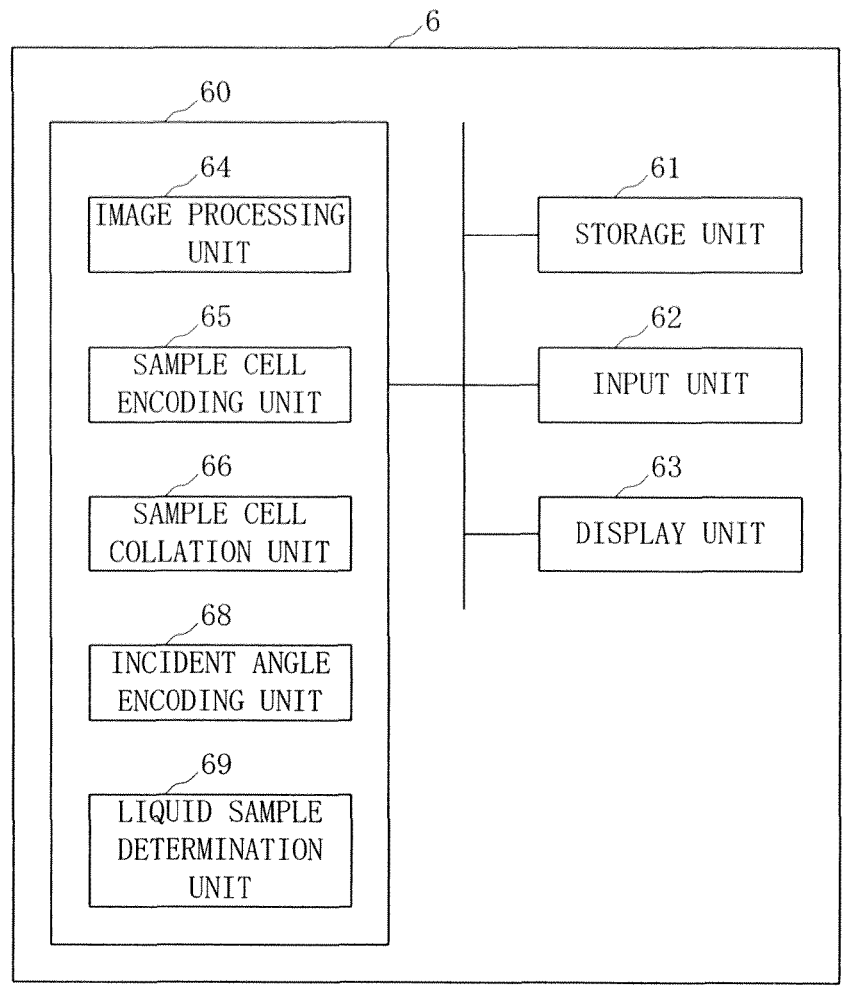
FIG. 32 is a block diagram exemplifying the arrangement of the data processing device of a surface plasmon resonance measuring device according to the 10th embodiment of the present invention.

FIG. 32 is a block diagram exemplifying the arrangement of the data processing device 6 in the 10th embodiment. The data processing device 6 includes a control unit 60, storage unit 61, input unit 62, and display unit 63.

The control unit 60 includes an image processing unit 64, sample cell encoding unit 65, sample cell collation unit 66, incident angle encoding unit 68, and liquid sample determination unit 69.

Figure 33:
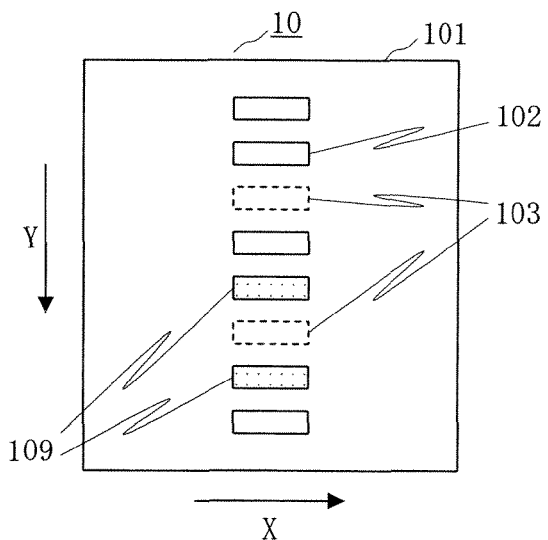
FIG. 33 is a plan view showing the structure of a sample cell used in the 10th embodiment of the present invention.
Figure 34:
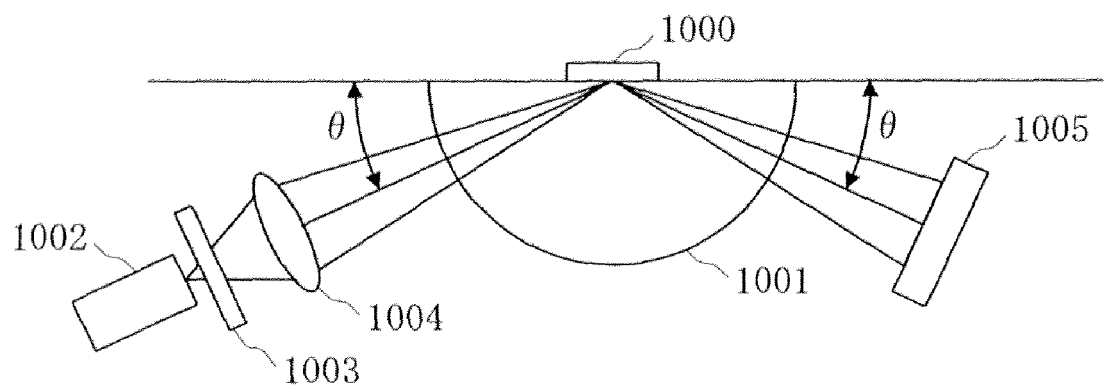
FIG. 34 is a block diagram showing the schematic arrangement of a conventional surface plasmon resonance measuring device.

FIG. 33 is a plan view showing the structure of a sample cell 10 used in the 10th embodiment. The 10th embodiment adopts the sample cell 10 having a metal thin film 101 formed on a transparent body 100, substance films 102 to be measured that are immobilized at substance-film-to-be-measured arrangement portions on the metal thin film 101, blank portions 103 having no substance film to be measured at a substance-film-to-be-measured arrangement portion, and liquid sample detection substance films 109 that are immobilized at detection substance film arrangement portions on the metal thin film 101 and change in refractive index depending on the property of a liquid sample. The sample cell 10 is set on the prism 1, with the substance films 102 to be measured and the liquid sample detection substance films 109 facing up and the transparent body 100 in contact with the prism 1.

The actions of the prism 1, light source 2, polarizing plate 3, condenser lens 4, CCD camera 5, database 7, pump 8, and channel 9 are the same as those described in the first to ninth embodiments.

Sample cell identification processing by the image processing unit 64, sample cell encoding unit 65, and sample cell collation unit 66 is the same as that explained in the first embodiment. Liquid sample appropriateness determination processing by the image processing unit 64, incident angle encoding unit 68, and liquid sample determination unit 69 is the same as that explained in the ninth embodiment. A description of these processes will not be repeated.

The 10th embodiment has exemplified a combination of the first and ninth embodiments. However, the present invention is not limited to this, and the second to eighth embodiments and the ninth embodiment may be properly combined.

The data processing device 6 in the first to 10th embodiments can be implemented by a computer having a CPU, storage device, and external interface, and a program for controlling these hardware resources. The computer is provided with a program for achieving the surface plasmon resonance measuring method of the present invention while the program is recorded on a recording medium such as a flexible disk, CD-ROM, DVD-ROM, or memory card. The CPU writes, in the storage device, the program loaded from the recording medium, and executes processes described in the first to 10th embodiments.

Note that the SPR measuring device in each of the first to 10th embodiments may include an Internet connection device. The database 7 may reside in the Internet server.

INDUSTRIAL APPLICABILITY

The present invention is applicable to a surface plasmon resonance measuring device.

The invention claimed is:

1. A surface plasmon resonance measuring device comprising:
    a light source which irradiates and excites surface plasmon resonance, with condensed light, a sample cell having a characteristic structure of reflectance of light that is formed in advance as an identification code of the sample cell from at least one of a substance film to be measured and a substance film different from the substance film to be measured on part of a metal thin film, from a surface opposite to a surface on which the substance film to be measured is immobilized to the metal thin film;
    a camera which detects light reflected by the sample cell; and
    encoding means for extracting the identification code from a feature of an image sensed by said camera.

2. A surface plasmon resonance measuring device according to claim 1, wherein the sample cell has, as the code for identifying a sample cell, a pattern of presence/absence of the substance film to be measured on the metal thin film, and said encoding means includes means for extracting the identification code based on the pattern of presence/absence of the substance film to be measured that is obtained from an image sensed by said camera.

3. A surface plasmon resonance measuring device according to claim 1, wherein the sample cell has, as the code for identifying a sample cell, a positional shift amount of the substance film to be measured from a specified position on the metal thin film, and said encoding means includes means for extracting the identification code based on the positional shift amount of the substance film to be measured from the specified position that is obtained from an image sensed by said camera.

4. A surface plasmon resonance measuring device according to claim 1, wherein the sample cell has, as the code for identifying a sample cell, a width of the substance film to be measured on the metal thin film, and said encoding means includes means for extracting the identification code based on the width of the substance film to be measured that is obtained from an image sensed by said camera.

5. A surface plasmon resonance measuring device according to claim 1, wherein the sample cell has, as the code for identifying a sample cell, at least one of a start position and end position of the substance film to be measured on the metal thin film, and said encoding means includes means for extracting the identification code based on at least one of the start position and end position of the substance film to be measured that is obtained from an image sensed by said camera.

6. A surface plasmon resonance measuring device according to claim 1, wherein the sample cell has, as the code for identifying a sample cell, a change of a minimum reflectance caused by a property control member which is buried in the substance film to be measured on the metal thin film and is different in imaginary part of refractive index from the substance film to be measured, and said encoding means includes means for extracting the identification code based on a minimum reflectance of an incident angle-reflectance curve that is obtained from an image sensed by said camera.

7. A surface plasmon resonance measuring device according to claim 1, wherein the sample cell has, as the code for identifying a sample cell, presence/absence of a reflectance valley based on a property control layer which is sandwiched between the metal thin film and the substance film to be measured and is lower in refractive index than the substance film to be measured, and said encoding means includes means for extracting the identification code based on presence/absence of a reflectance valley of an incident angle-reflectance curve that is obtained from an image sensed by said camera.

8. A surface plasmon resonance measuring device according to claim 1, wherein the sample cell has, as the code for identifying a sample cell, a film thickness pattern of the substance film to be measured on the metal thin film, and said encoding means includes means for extracting the identification code based on a reflectance pattern of an incident angle-reflectance curve that is obtained from an image sensed by said camera.

9. A surface plasmon resonance measuring device according to claim 1, further comprising:
  a database in which identification code for identifying a sample cell and array information of substance films to be measured on the sample cell are registered in advance in correspondence with each other; and
  sample cell collation means for acquiring, from said database, array information of a sample cell having a code coincident with a code extracted by said encoding means.

10. A surface plasmon resonance measuring device according to claim 1, further comprising:
  a database in which the identifying code for the sample cell and manufacturing date & time information of the sample cell are registered in advance in correspondence with each other; and
  sample cell determination means for acquiring, from said database, manufacturing date & time information of a sample cell having a code coincident with a code extracted by said encoding means, and determining a valid period of the sample cell.

11. A surface plasmon resonance measuring device according to claim 1, further comprising sample cell determination means for determining, based on a code extracted by said encoding means, whether the sample cell is attached appropriately.

12. A surface plasmon resonance measuring device according to claim 1, further comprising:
  a pump which supplies a liquid sample onto a surface of the sample cell on which the substance film to be measured is immobilized; and
  liquid sample determination means for determining, based on a code extracted by said encoding means, whether the liquid sample is appropriate, wherein the sample cell is obtained by immobilizing, on the metal thin film, a liquid sample detection substance film whose refractive index changes depending on a property of the liquid sample.

13. A surface plasmon resonance measuring device according to claim 12, wherein said encoding means includes:
  image processing means for obtaining, from an image sensed by said camera, a correlation between an incident angle and reflectance of light with respect to at least the substance film to be measured and the liquid sample detection substance film; and
  incident angle encoding means for encoding an incident angle of light at which a minimum reflectance is obtained from the correlation between the incident angle and the reflectance.

14. A surface plasmon resonance measuring device according to claim 12, further comprising a database in which a code to be output from said encoding means when a normal liquid sample reacts with the liquid sample detection substance film is registered in advance, wherein, when a code extracted by said encoding means after introducing the liquid sample to the sample cell is registered in said database, said liquid sample determination means determines that a normal liquid sample has been supplied.

15. A surface plasmon resonance measuring device according to claim 12, wherein the liquid sample detection substance film is one of a substance film which is reduced upon reaction with the liquid sample, a substance film which disappears upon reaction with the liquid sample, and a substance film whose refractive index changes upon reaction with the liquid sample.

16. A sample cell for measuring surface plasmon resonance, comprising a characteristic structure of reflectance of light that is formed in advance as an identification code of the sample cell from at least one of a substance film to be measured via surface plasmon resonance and a substance film different from the substance film to be measured via surface plasmon resonance on part of a metal thin film.

17. A sample cell for measuring surface plasmon resonance according to claim 16, wherein a pattern of presence/absence of the substance film to be measured on the metal thin film serves as the code for identifying a sample cell.

18. A sample cell for measuring surface plasmon resonance according to claim 16, wherein a positional shift amount of the substance film to be measured from a specified position on the metal thin film serves as the identification code for the sample cell.

19. A sample cell for measuring surface plasmon resonance according to claim 16, wherein a width of the substance film to be measured on the metal thin film serves as the identification code for the sample cell.

20. A sample cell for measuring surface plasmon resonance according to claim 16, wherein at least one of a start position and end position of the substance film to be measured on the metal thin film serves as the identification code for the sample cell.

21. A sample cell for measuring surface plasmon resonance according to claim 16, wherein a change of a minimum reflectance caused by a property control member which is buried in the substance film to be measured on the metal thin film and is different in imaginary part of refractive index from the substance film to be measured serves as the identification code for identifying the sample cell.

22. A sample cell for measuring surface plasmon resonance according to claim 16, wherein presence/absence of a reflectance valley based on a property control layer which is sandwiched between the metal thin film and the substance film to be measured and is lower in refractive index than the substance film to be measured serves as the identification code for the sample cell.

23. A sample cell for measuring surface plasmon resonance according to claim 16, wherein a film thickness pattern of the substance film to be measured on the metal thin film serves as the identifying code for the sample cell.

24. A sample cell for measuring surface plasmon resonance according to claim 16, wherein a liquid sample detection substance film whose refractive index changes depending on a property of a liquid sample introduced onto the sample cell is immobilized on the metal thin film.

25. A sample cell for measuring surface plasmon resonance according to claim 24, wherein the liquid sample detection substance film is one of a substance film which is reduced upon reaction with the liquid sample, a substance film which disappears upon reaction with the liquid sample, and a substance film whose refractive index changes upon reaction with the liquid sample.

26. A surface plasmon resonance measuring method comprising:
    the irradiation step of irradiating and exiting surface plasmon resonance, with condensed light, a sample cell having a characteristic structure of reflectance of light that is formed in advance as an identification code of the sample cell from at least one of a substance film to be measured and a substance film different from the substance film to be measured on part of a metal thin film, from a surface opposite to a surface on which the substance film to be measured is immobilized to the metal thin film;
    the image sensing step of detecting light reflected by the sample cell; and
    the encoding step of extracting the identification code from a feature of an image sensed in the image sensing step.

27. A surface plasmon resonance measuring method according to claim 26, further comprising:
    the introduction step of introducing a liquid sample onto a surface of the sample cell on which the substance film to be measured is immobilized; and
    the liquid sample determination step of determining, based on a code extracted in the encoding step, whether the liquid sample is appropriate, wherein the sample cell is obtained by immobilizing, on the metal thin film, a liquid sample detection substance film whose refractive index changes depending on a property of the liquid sample.

* * * * *